(12) United States Patent
    Ohta (10) Patent No.: US 11,534,129 B2
(45) Date of Patent: Dec. 27, 2022

(54) RADIATION IMAGING SYSTEM AND RADIATION IMAGING APPARATUS

(71) Applicant: CANON KABUSHIKI KAISHA, Tokyo (JP)

(72) Inventor: Koichi Ohta, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 56 days.

(21) Appl. No.: 17/330,742

(22) Filed: May 26, 2021

(65) Prior Publication Data

US 2021/0378621 A1    Dec. 9, 2021

(30) Foreign Application Priority Data

Jun. 5, 2020   (JP) .............................. JP2020-098882

(51) Int. Cl.
    *A61B 6/00*    (2006.01)
    *G01N 23/04*   (2018.01)
(52) U.S. Cl.
    CPC .............. *A61B 6/542* (2013.01); *A61B 6/563* (2013.01); *G01N 23/04* (2013.01); *G01N 2223/304* (2013.01)
(58) Field of Classification Search
    CPC ........... A61B 6/542; A61B 6/563; A61B 6/54; A61B 6/56; G01N 23/04; G01N 2223/304; G01N 2223/30
    See application file for complete search history.

(56) References Cited

U.S. PATENT DOCUMENTS

| 2013/0148784 A1 | 6/2013 | Tajima |
| 2013/0223592 A1* | 8/2013 | Sato ...................... A61B 6/542 378/97 |
| 2019/0230299 A1 | 7/2019 | Ohta |

FOREIGN PATENT DOCUMENTS

JP          2014-90863 A     5/2014

* cited by examiner

*Primary Examiner* — Courtney D Thomas
(74) *Attorney, Agent, or Firm* — Venable LLP (57) ABSTRACT

A radiation imaging system is provided. The system comprises a radiation imaging apparatus including a plurality of pixels for acquiring radiation image data and a detection unit for performing exposure control during radiation irradiation, and a radiation control apparatus configured to control a radiation source that irradiates radiation to the radiation imaging apparatus. The radiation imaging apparatus and the radiation control apparatus transmit signals that relate to exposure control by wireless communication. The radiation imaging apparatus, in a case where an irradiation stop signal indicating that radiation irradiation has been stopped is not received from the radiation control apparatus after a signal instructing to stop radiation irradiation has been transmitted to the radiation control apparatus and until a first time interval has elapsed, transmits a signal instructing to stop radiation irradiation to the radiation control apparatus again.

20 Claims, 5 Drawing Sheets

RADIATION IMAGING SYSTEM AND RADIATION IMAGING APPARATUS

BACKGROUND OF THE INVENTION

Field of the Invention

The present invention is related to a radiation imaging system and a radiation imaging apparatus.

DESCRIPTION OF THE RELATED ART

In medical imaging diagnosis or non-destructive inspection, radiation imaging apparatuses that use a flat plane detector (a flat panel detector, FPD) configured by a semiconductor material are widely used. A technique of monitoring radiation incident on the radiation imaging apparatuses is known. By detecting the dose of radiation in real time, it becomes possible to detect a start and an end of radiation irradiation as well as know the integrated dose of radiation incident during radiation irradiation and then perform Automatic Exposure Control (AEC). In Japanese Patent Laid-Open No. 2014-090863, a radiation imaging system in which a radiation imaging apparatus that transmits, to an interface apparatus for each predetermined transmission timing, dose information indicating the dose of radiation detected during radiation irradiation is described. The interface apparatus, by adjusting the dose information such that errors caused by wireless communication delays are reduced, enables exposure control that prevents the effect of wireless communication delays.

SUMMARY OF THE INVENTION

Wireless communication environments are not always stable and significantly change depending on noise caused by an operation of other wireless communication devices and medical devices such as a microwave therapy device, and cases where wireless communication connections are intermittently disconnected, where communication speed decreases, and the like may occur. In the radiation imaging system of Japanese Patent Laid-Open No. 2014-090863, when wireless communication connection becomes unstable during use of exposure control functions, some of the dose information that is transmitted a plurality of times or some of the individual dose information may not reach the interface apparatus. In a case where the dose information does not reach the interface apparatus, there is a possibility that exposure control accuracy will decrease.

Some embodiments of the present invention provide a technique that is advantageous for preventing deterioration of accuracy in exposure control caused by communication problems in a radiation imaging system and a radiation imaging apparatus that perform exchange of signals for exposure control using wireless communication.

According to some embodiments, a radiation imaging system comprising: a radiation imaging apparatus including a plurality of pixels for acquiring radiation image data and a detection unit for performing exposure control during radiation irradiation; and a radiation control apparatus configured to control a radiation source that irradiates radiation to the radiation imaging apparatus, wherein the radiation imaging apparatus and the radiation control apparatus transmit signals that relate to exposure control by wireless communication, and the radiation imaging apparatus, in a case where an irradiation stop signal indicating that radiation irradiation has been stopped is not received from the radiation control apparatus after a signal instructing to stop radiation irradiation has been transmitted to the radiation control apparatus and until a first time interval has elapsed, transmits a signal instructing to stop radiation irradiation to the radiation control apparatus again, is provided.

According to some other embodiments, a radiation imaging apparatus comprising: a plurality of pixels for acquiring radiation image data; and a detection unit for performing exposure control during radiation irradiation, wherein the radiation imaging apparatus, in a case where an irradiation stop signal indicating that radiation irradiation has been stopped is not received from an external apparatus after a signal instructing to stop radiation irradiation has been transmitted to the external apparatus by wireless communication and until a first time interval has elapsed, transmits a signal instructing to stop radiation irradiation to the external apparatus again, is provided.

Further features of the present invention will become apparent from the following description of exemplary embodiments (with reference to the attached drawings).

DESCRIPTION OF THE EMBODIMENTS

Hereinafter, embodiments will be described in detail with reference to the attached drawings. Note, the following embodiments are not intended to limit the scope of the claimed invention. Multiple features are described in the embodiments, but limitation is not made to an invention that requires all such features, and multiple such features may be combined as appropriate. Furthermore, in the attached drawings, the same reference numerals are given to the same or similar configurations, and redundant description thereof is omitted.

In addition, radiation according to the present invention can include not only α-rays, β-rays, and γ-rays that are beams generated by particles (including photons) emitted by radioactive decay but also beams having the same amount of or more energy, for example, X-rays, particle rays, and cosmic rays.

Figure 1:
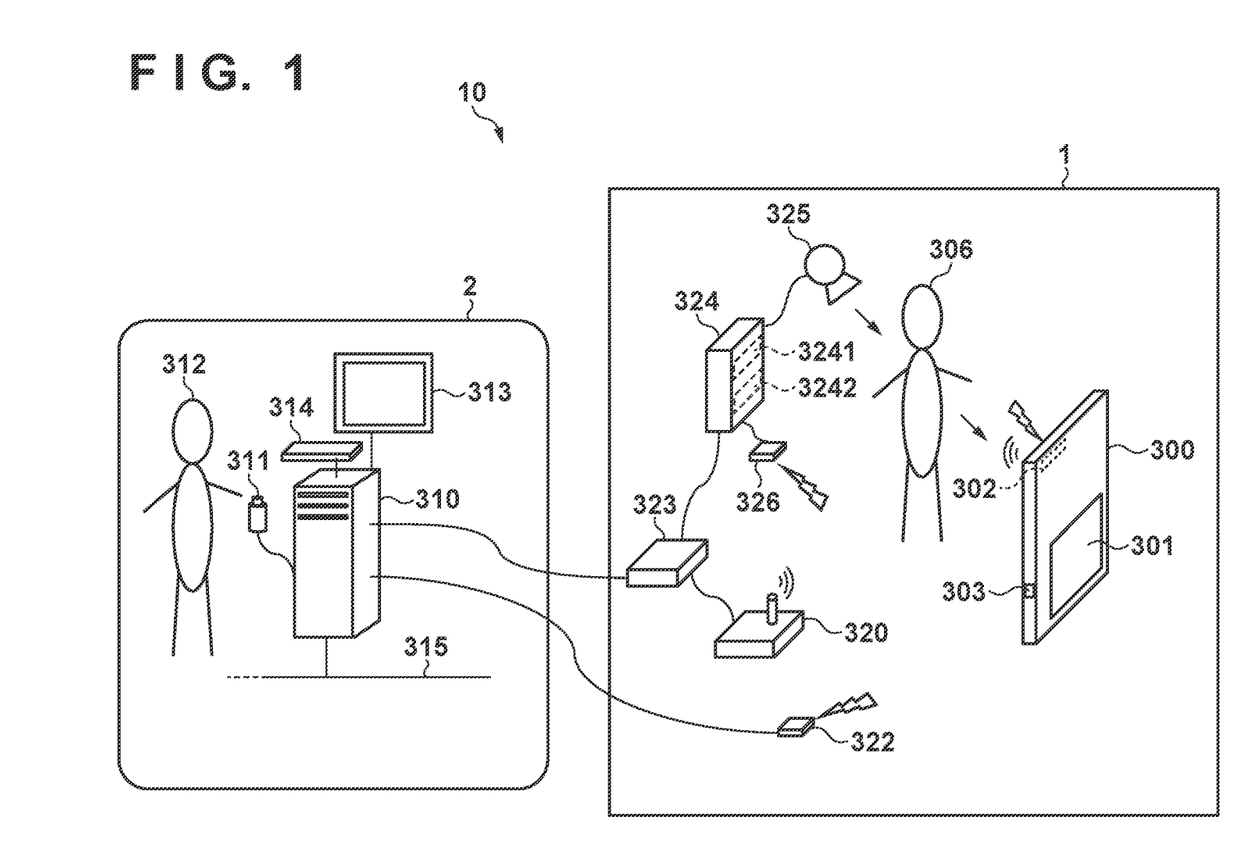
FIG. 1 is a view illustrating an example of a configuration of a radiation imaging system according to the present embodiment.

A configuration and operation of a radiation imaging system according to the present embodiment will be described with reference to FIGS. 1 to 5. FIG. 1 is a view illustrating an example of a configuration of a radiation imaging system 10 according to the present embodiment. In the present embodiment, the radiation imaging system 10 irradiates radiation onto a subject and is disposed in a radiation room 1 in which radiation image imaging is performed and a control room 2, which is positioned in the vicinity of the radiation room 1.

In the radiation room 1, a radiation imaging apparatus 300, a wireless access point 320, an interface box 323, a radiation control apparatus 324, and a radiation source 325 of the radiation imaging system 10 are disposed. Also, in the radiation room 1, an entry apparatus 322 and cables that connect each component are disposed. In the control room 2, a main control apparatus 310, a radiation irradiation switch 311, a display apparatus 313, an input apparatus 314, and an in-hospital LAN 315 of the radiation imaging system 10 are disposed.

The radiation imaging apparatus 300 includes a power supply control unit 301 configured by a battery and the like, a wireless communication unit 302, and a switch 303. The radiation imaging apparatus 300 detects radiation that has passed through a subject 306 and then generates radiation image data. Also, the radiation imaging apparatus 300 includes a detection unit for performing exposure control during radiation irradiation.

The wireless access point 320 is an access point for performing wireless communication such as wireless LAN typified by IEEE 802.11 and performs wireless communication with the wireless communication unit 302 of the radiation imaging apparatus 300. In the radiation imaging system 10, the wireless access point 320 can be used for relaying communication between the radiation imaging apparatus 300 and the main control apparatus 310 and the radiation imaging apparatus 300 and the radiation control apparatus 324.

The entry apparatus 322 performs communication with the wireless communication unit 302 of the radiation imaging apparatus 300. The interface box 323 control so as to enable communication between each of the wireless access point 320, the radiation control apparatus 324, and the main control apparatus 310. Also, the interface box 323 may comprise a function for supplying power to the radiation imaging apparatus 300 via a cable (not shown), a wired communication interface, and the like. The interface box 323 may be connected with the radiation control apparatus 324 by a dedicated interface cable. The interface box 323, depending on an interface that the radiation control apparatus 324 side can take, may connect using a general-purpose communication interface such as Ethernet. The interface box 323 may be replaced by a plurality of apparatuses such as an individual switching HUB, an interface box of the radiation control apparatus 324, and a power supply box.

The radiation control apparatus 324 controls the radiation source 325 and then irradiates radiation onto the subject 306. The radiation control apparatus 324 includes a radiation source control unit 3241 that controls the radiation source 325 so as to irradiate radiation based on a predetermined condition, and a generation control unit 3242 that controls generation of radiation of the radiation source 325 by signals indicating a start or a stoppage of irradiation from the radiation imaging apparatus 300. In the configuration illustrated in FIG. 1, the radiation source control unit 3241 and the generation control unit 3242 are illustrated in an integrated configuration; however, each of the radiation source control unit 3241 and the generation control unit 3242 may be separately configured. Also, the radiation control apparatus 324 comprises a wireless unit 326 for performing wireless communication with the wireless communication unit 302 of the radiation imaging apparatus 300. The wireless unit 326 may be embedded in the radiation control apparatus 324 or may be separate from the radiation control apparatus 324 as illustrated in FIG. 1.

The main control apparatus 310 controls the radiation imaging apparatus 300 and the radiation control apparatus 324. The main control apparatus 310, by communicating with the radiation control apparatus 324 (the generation control unit 3242) and the radiation imaging apparatus 300 via the interface box 323, can comprehensively control the entire the radiation imaging system 10.

The radiation irradiation switch 311, by the operation of an operator 312, inputs timings of radiation irradiation. The input apparatus 314 is an apparatus that performs input of instructions from the operator 312, and various input devices such as a keyboard and a touch panel are used. The display apparatus 313 is an apparatus that performs display of image-processed radiation image data and a GUI, and a display and the like are used. The in-hospital LAN 315 is a backbone network in a medical facility. For example, the in-hospital LAN 315 may be Hospital Information Systems (HIS) or Radiology Information Systems (RIS). In the present embodiment, an example of construction of a system in which the radiation imaging system 10 is constructed by a local network and is separated from the in-hospital LAN 315 is described; however, the radiation imaging system 10 may be constructed by a network that is directly connect to the in-hospital LAN 315.

Next, an operation of the radiation imaging system 10 will be described. First, the operator 312 performs an operation of registering the radiation imaging apparatus 300 into the radiation imaging system 10. When the switch 303 of the radiation imaging apparatus 300 is pressed by the operator 312, communication between the radiation imaging apparatus 300 and the main control apparatus 310 via the entry apparatus 322 is started.

The main control apparatus 310 transmits information for performing communication via the wireless access point 320 to the radiation imaging apparatus 300 via the entry apparatus 322. In other words, communication via the entry apparatus 322 transmits setting information for performing communication via the wireless access point 320. The setting information, in a case where communication via the wireless access point 320 performs communication using the wireless LAN, includes, for example, a communication method such as IEEE 802.11n, a physical channel, an ESSID, an encryption key, and the like as well as information such as an IP address to be set for the radiation imaging apparatus 300. Also, the setting information may include information for performing communication between the radiation imaging apparatus 300 and the radiation control apparatus 324 via the wireless unit 326. Also, the radiation imaging apparatus 300, by using communication via the entry apparatus 322, may transmit apparatus information of the radiation imaging apparatus 300 to the main control apparatus 310. The apparatus information includes, for example, information such as a unique ID for identifying the radiation imaging apparatus 300, a MAC address, executable image capturing modes, a usage history, and fault states. Based on this apparatus information, the radiation imaging apparatus 300 may be registered into the radiation imaging system 10. For example, in a case of using the radiation imaging apparatus 300 in a radiation imaging system different from the radiation imaging system 10, the above registration operation is conducted each time.

The switch 303 that fulfills the function of triggering the registration operation does not necessarily need to be comprised by the radiation imaging apparatus 300 and may be comprised by the entry apparatus 322. Also, the switch 303 may be comprised on a GUI that the main control apparatus 310 displays on the display apparatus 313.

It is often the case that the radiation image data generated by an imaging operation is uncompressed RAW data, and there are cases where the amount of data becomes several megabytes to several tens of megabytes. The radiation image data is transmitted from the radiation imaging apparatus 300 to the main control apparatus 310 and then displayed on the display apparatus 313; therefore, it is necessary to transmit a large amount of data at a high speed. Accordingly, high-speed communication such as wireless LAN is used for wireless communication via the wireless access point 320.

The radiation imaging apparatus 300 sets a configuration of the wireless communication unit 302 in accordance with the setting information received from the main control apparatus 310. By this, the radiation imaging apparatus 300 establishes a wireless communication connection between the wireless access point 320 and the wireless communication unit 302.

The wireless communication unit 302 may support a plurality of kinds of wireless communication. For example, the wireless communication unit 302 may perform communication with the wireless access point 320 using a wireless LAN and perform wireless communication with the entry apparatus 322 and the wireless unit 326 using a communication method other than a wireless LAN. For example, the wireless communication unit 302 may perform communication that uses Bluetooth® or infrared light to and from the entry apparatus 322 and the wireless unit 326.

In the present embodiment, communication with the radiation imaging apparatus 300 and the main control apparatus 310 via the wireless access point 320 is established using communication via the entry apparatus 322 as described above; however, the present invention is not limited to this. For example, the radiation imaging apparatus 300 and the main control apparatus 310 may directly perform transmission of the setting information and the apparatus information via the wireless access point 320. Also, communication between the radiation imaging apparatus 300 and the radiation control apparatus 324 is not limited to being performed via the wireless communication unit 302 and the wireless unit 326. For example, communication between the radiation imaging apparatus 300 and the radiation control apparatus 324 may be performed via the interface box 323 and the wireless access point 320. In a case where all of the communications between the radiation imaging apparatus 300, the main control apparatus 310, and the radiation control apparatus 324 are performed via the interface box 323, the entry apparatus 322 and the wireless unit 326 does not need to be disposed in the radiation imaging system 10.

Next, the operator 312 inputs subject information such as an ID, a name, and the date of birth of the subject 306 and a body part to be image of the subject 306 into the main control apparatus 310. After inputting the body part to be image, the operator 312 secures the posture of the subject 306 and the radiation imaging apparatus 300. When imaging preparation is completed, the operator 312 presses the radiation irradiation switch 311. When the radiation irradiation switch 311 is pressed, radiation may be irradiated from the radiation source 325 toward the subject 306.

The radiation imaging apparatus 300, by performing wireless communication with the radiation control apparatus 324 (the generation control unit 3242), may perform control such as starting or ending radiation irradiation. The radiation irradiated onto the subject 306 passes through the subject 306 and then irradiates the radiation imaging apparatus 300. The radiation imaging apparatus 300, for example, converts the incident radiation into visible light and then detects the result as a radiation image signal in a photoelectric conversion element.

The radiation imaging apparatus 300, by driving the photoelectric conversion element, reads out the radiation image signal, and then, by converting an analog signal into a digital signal in an AD conversion circuit, acquires digital radiation image data. The radiation imaging apparatus 300 transmits the acquired radiation image data to the main control apparatus 310 via wireless communication. In the present embodiment, an example in which the radiation imaging apparatus 300 and the main control apparatus 310 perform transmission of the radiation image data via wireless communication is described; however, the present invention is not limited to this. A configuration may be taken such that the interface box 323 comprises a cable and the like to connect to the radiation imaging apparatus 300 and the radiation image data is transmitted from the radiation imaging apparatus 300 to the main control apparatus 310 by wired communication.

The main control apparatus 310 performs image processing of the received radiation image data. The main control apparatus 310 displays the radiation image based on the image-processed radiation image data on the display apparatus 313. As described above, the main control apparatus 310 may function as an image processing apparatus and a display control apparatus. The above is an operation of the radiation imaging system from when the operator 312 registers the radiation imaging apparatus 300 into the radiation imaging system 10 until the radiation image of the subject 306 is displayed on the display apparatus 313.

Figure 2:
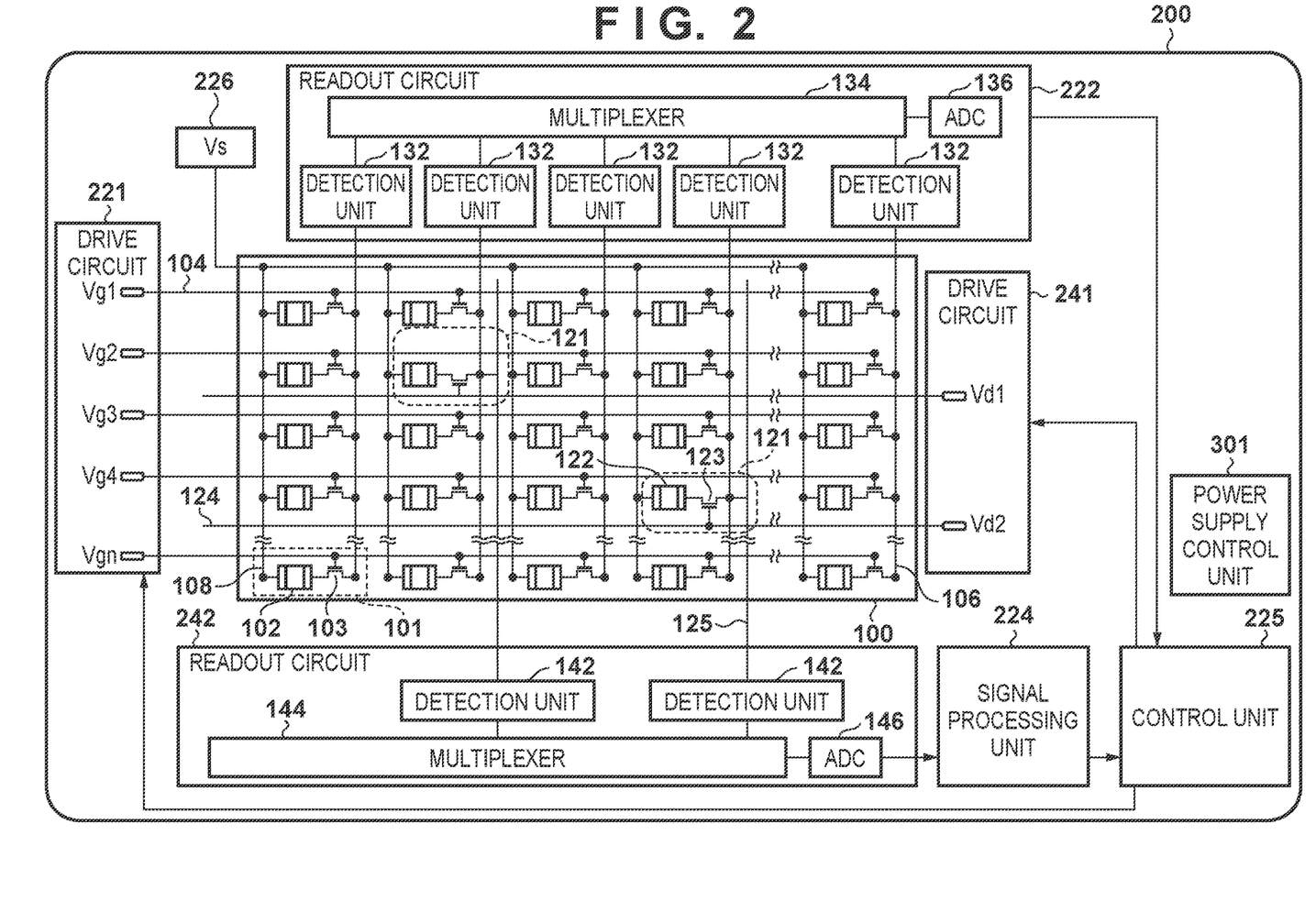
FIG. 2 is a view illustrating an example of a configuration a radiation imaging apparatus disposed in the radiation imaging system of FIG. 1.

Here, a configuration of the radiation imaging apparatus 300 will be described using FIG. 2. As illustrated in FIG. 2, the radiation imaging apparatus 300 has a radiation detector 100. The radiation detector 100 has a function of detecting irradiated radiation. The radiation detector 100 has a plurality of pixels for acquiring the radiation image data disposed so as to configure a plurality of columns and a plurality of rows. In the description below, a region in which the plurality of pixels have been positioned in the radiation detector 100 will be an imaging region. The plurality of pixels include a plurality of imaging pixels 101 for acquiring the radiation image and detection pixels 121 for monitoring radiation irradiation. As detection units for performing exposure control during radiation irradiation, the detection pixels 121 are used. In other words, the detection units for performing exposure control are disposed in the imaging region (the radiation detector 100).

The imaging pixels 101 include a conversion element 102 that converts radiation into an electrical signal and a switch 103 disposed between a column signal line 106 and the conversion element 102. The detection pixels 121 include a conversion element 122 that converts radiation into an electrical signal and a switch 123 disposed between a detection signal line 125 and the conversion element 122. The detection pixels 121 are disposed in the same column as some of the plurality of imaging pixels 101.

In the present embodiment, the conversion elements 102 and the conversion elements 122 are configured by a scintillator that converts radiation into light and a photoelectric conversion element that converts light into electrical signals. A scintillator, for example, may be formed in a sheet form so as to cover the imaging region and shared by a plurality of pixels. Also, the conversion elements 102 and the conversion elements 122 may be configured by conversion elements that convert radiation directly into electrical signals.

The switches 103 and the switches 123 include, for example, thin-film transistors (TFT) whose active regions have been configured by semiconductors such as amorphous silicon and polycrystalline silicon. In the present embodiment, polycrystalline silicon is used for the active regions.

The radiation imaging apparatus 300 includes a plurality of column signal lines 106 and a plurality of drive lines 104. Each of the column signal lines 106 corresponds to one column of a plurality of columns in the imaging region. Each of the drive lines 104 corresponds to one row of a plurality of rows in the imaging region. The drive lines 104 are driven by a drive circuit 221.

One of two electrodes of the conversion element 102 is connected to one of the main electrodes of the switch 103 and the other of two electrodes of the conversion element 102 is connected to a bias line 108. Here, the bias line 108 extends in a column direction and is connected to all the electrodes of a plurality of conversion elements 102 disposed in a column direction.

A bias voltage Vs is supplied from an element power supply circuit 226 to the bias lines 108. The power supply control unit 301 is configured including a battery, a DC/DC converter, and the like. The power supply control unit 301 includes the element power supply circuit 226 and generates power for analog circuits and power for digital circuit for performing drive control, wireless communication, and the like.

The other main electrodes of the switches 103 of the plurality of imaging pixels 101 configuring one column are connected to the column signal lines 106. Control electrodes of the switches 103 of the plurality of imaging pixels 101 configuring one row are connected to a shared drive line 104. The plurality of column signal lines 106 are connected to a readout circuit 222. Here, the readout circuit 222 includes detection units 132, a multiplexer 134, and an analog/digital converter (AD converter) 136.

Each of the plurality of column signal lines 106 are connected to a corresponding detection unit 132 of the plurality of detection units 132 disposed in the readout circuit 222. In this case, one column signal line 106 corresponds to one detection unit 132. The detection units 132 include, for example, differential amplifiers. The multiplexer 134 selects the plurality of detection units 132 in a predetermined order and supplies a signal from the selected detection unit 132 to the AD converter 136. The AD converter 136 converts the supplied signal into a digital signal and outputs it.

One of two electrodes of the conversion element 122 is connected to one of the main electrodes of the switch 123 and the other of two electrodes of the conversion element 122 is connected to the bias line 108. The other main electrodes of the switches 123 are connected to the detection signal lines 125. The control electrodes of the switches 123 are electrically connected to drive lines 124.

In the radiation imaging apparatus 300, one detection signal line 125 may be disposed, or as illustrated in FIG. 2, a plurality of detection signal lines 125 may be disposed. One or the plurality of detection pixels 121 are connected to one detection signal line 125. The drive lines 124 are driven by a drive circuit 241. One or the plurality of detection pixels 121 are connected to one drive line 124. The detection signal lines 125 are connected to a readout circuit 242. Here, the readout circuit 242 includes a detection unit 142, a multiplexer 144, and an AD converter 146.

Each of the plurality of detection signal lines 125 are connected to a corresponding detection unit 142 of the plurality of detection units 142 of the readout circuit 242. Here, one detection signal line 125 corresponds to one detection unit 142. The detection units 142 include, for example, a differential amplifier. The multiplexer 144 selects the plurality of detection units 142 in a predetermined order, and supplies a signal from the selected detection unit 142 to the AD converter 146. The AD converter 146 converts the supplied signal into a digital signal and outputs it. The output from the readout circuit 242 (the AD converter 146) is supplied to a signal processing unit 224 and then is processed by the signal processing unit 224. The signal processing unit 224, based on the output of the readout circuit 242 (the AD converter 146), outputs information indicating radiation irradiation related to the radiation imaging apparatus 300. Specifically, the signal processing unit 224, for example, detects radiation irradiation related to the radiation imaging apparatus 300 and also calculates the amount of radiation irradiation and/or the integrated dose and then uses it in exposure control.

A control unit 225, based on information from the signal processing unit 224 and control commands from the main control apparatus 310, controls each component of the radiation imaging apparatus 300 such as the drive circuit 221, the drive circuit 241, the readout circuits 222 and 242.

Next, an operation of exposure control of the radiation imaging system 10 using the radiation imaging apparatus 300 will be described. The operator 312 inputs a dose, the maximum irradiation time, a tube current, a tube voltage, a radiation detection region (ROI) which is a region for which radiation should be monitored, body part information, and the like into the main control apparatus 310. The main control apparatus 310 transmits to the radiation imaging apparatus 300 and the radiation control apparatus 324 (the generation control unit 3242) the radiation irradiation conditions, the radiation detection region (ROI), the body part information, and the like that were inputted. When imaging preparation is completed and the operator 312 presses the radiation irradiation switch 311, radiation is irradiated. The irradiated radiation passes through the subject 306 and then irradiates the radiation imaging apparatus 300. The radiation imaging apparatus 300 detects radiation incident on the radiation detection region (ROI) using the detection pixels 121 and then calculates the integrated dose, which is an accumulated value of the dose (reached dose) detected in the signal processing unit 224. Here, the control unit 225 calculates a proper dose from the integrated dose information from the signal processing unit 224, the body part information and the imaging conditions that the operator 312 inputted, and the like and then decides a timing to stop radiation irradiation.

The radiation imaging apparatus 300, based on the decided timing to stop radiation irradiation, transmits a signal instructing to stop radiation irradiation to the radiation control apparatus 324 via the wireless communication unit 302 and the wireless unit 326. The radiation control apparatus 324 (the generation control unit 3242), based on the notified timing to stop radiation irradiation, stops radiation irradiation from the radiation source 325. In the present embodiment, the radiation imaging apparatus 300 calculates the amount of radiation irradiation and then notifies the timing to stop radiation irradiation; however, the present invention is not limited to this. A configuration may be such that the radiation imaging apparatus 300 transmits the reached dose for each predetermined time as a detection result to the radiation control apparatus 324 (the generation control unit 3242) and then the radiation control apparatus 324 calculates the accumulated value of the reached dose.

In relation to the timing to stop radiation irradiation decided in the radiation imaging apparatus 300, delays need to be prevented for signals related to exposure control transmitted from the radiation imaging apparatus 300 to the radiation control apparatus 324. In wireless communication environment of the radiation imaging system 10, there are cases where there is electromagnetic noise due to various reasons, and these can obstruct wireless communication. Also, for example, in a case where in a communication system that uses a wireless LAN, a channel setting policy of another wireless LAN communication system does not match, there are cases where communication is hindered due to wireless frequency bands that they use interfering. When affected as such, there is a possibility that an exposure control signal instructing the timing to stop radiation irradiation does not reach the radiation control apparatus 324 at an expected timing.

Figure 3:
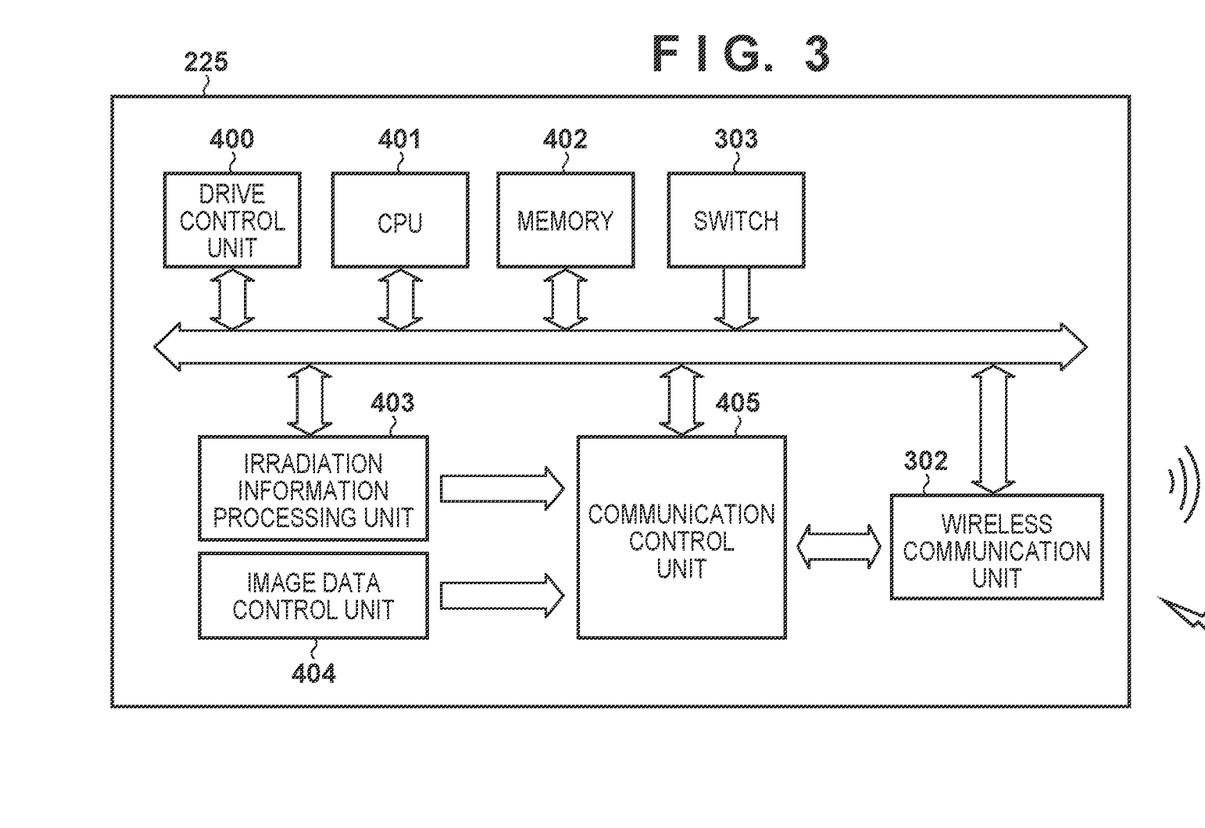
FIG. 3 is a view illustrating an example of a configuration of a control unit of the radiation imaging apparatus of FIG. 2.

FIG. 3 is a view illustrating an example of a configuration of the control unit 225 of the radiation imaging apparatus 300. As illustrated in FIG. 3, the control unit 225 includes a drive control unit 400, a CPU 401, a memory 402, an irradiation information processing unit 403, and an image data control unit 404. The control unit 225 further includes a communication control unit 405, the switch 303, and the wireless communication unit 302. The communication control unit 405 can wirelessly communicate with external apparatuses such as the radiation control apparatus 324 via the wireless communication unit 302 and can transmit/receive various kinds of information to and from the radiation control apparatus 324 and the like.

The drive control unit 400, based on information from the signal processing unit 224 and commands received from the main control apparatus 310, controls the drive circuit 221, the drive circuit 241, and the readout circuit 222. The CPU 401 performs control of the entire radiation imaging apparatus 300 using programs and various kinds of data stored in the memory 402. For example, the memory 402 stores programs and various kinds of data to be used when the CPU 401 executes processing. Also, in the memory 402, various kinds of data and radiation image data acquired by the processing of the CPU 401 may be stored. The wireless communication unit 302, when the operator 312 presses the switch 303, starts wireless communication with the entry apparatus 322 and then receives the above setting information and the like. The received information is stored in the memory 402 and, as described above, is used in setting of the wireless communication unit 302 for performing communication with the wireless access point 320 as appropriate.

The irradiation information processing unit 403 controls wireless communication with the radiation control apparatus 324 based on information from the signal processing unit 224 and information from the drive control unit 400. The irradiation information processing unit 403 and the radiation control apparatus 324 perform, via the wireless communication unit 302 and the wireless unit 326, transmission of information (e.g., a start of radiation irradiation, a stoppage notification, the amount of radiation irradiation, the integrated dose, and the like) that relates to control of the radiation control apparatus 324. The irradiation information processing unit 403 and the radiation control apparatus 324 may perform, via the wireless communication unit 302, the wireless access point 320, and the interface box 323, transmission of information that relates to control of the radiation control apparatus 324. The image data control unit 404 controls wireless communication of the main control apparatus 310 in addition to saving the image data from the readout circuit 222 in the memory 402. The image data control unit 404 and the main control apparatus 310 performs, via the wireless communication unit 302, the wireless access point 320, and the interface box 323, transmission of information (e.g., control commands and the like) that relates to control of the radiation image data.

Figure 4:
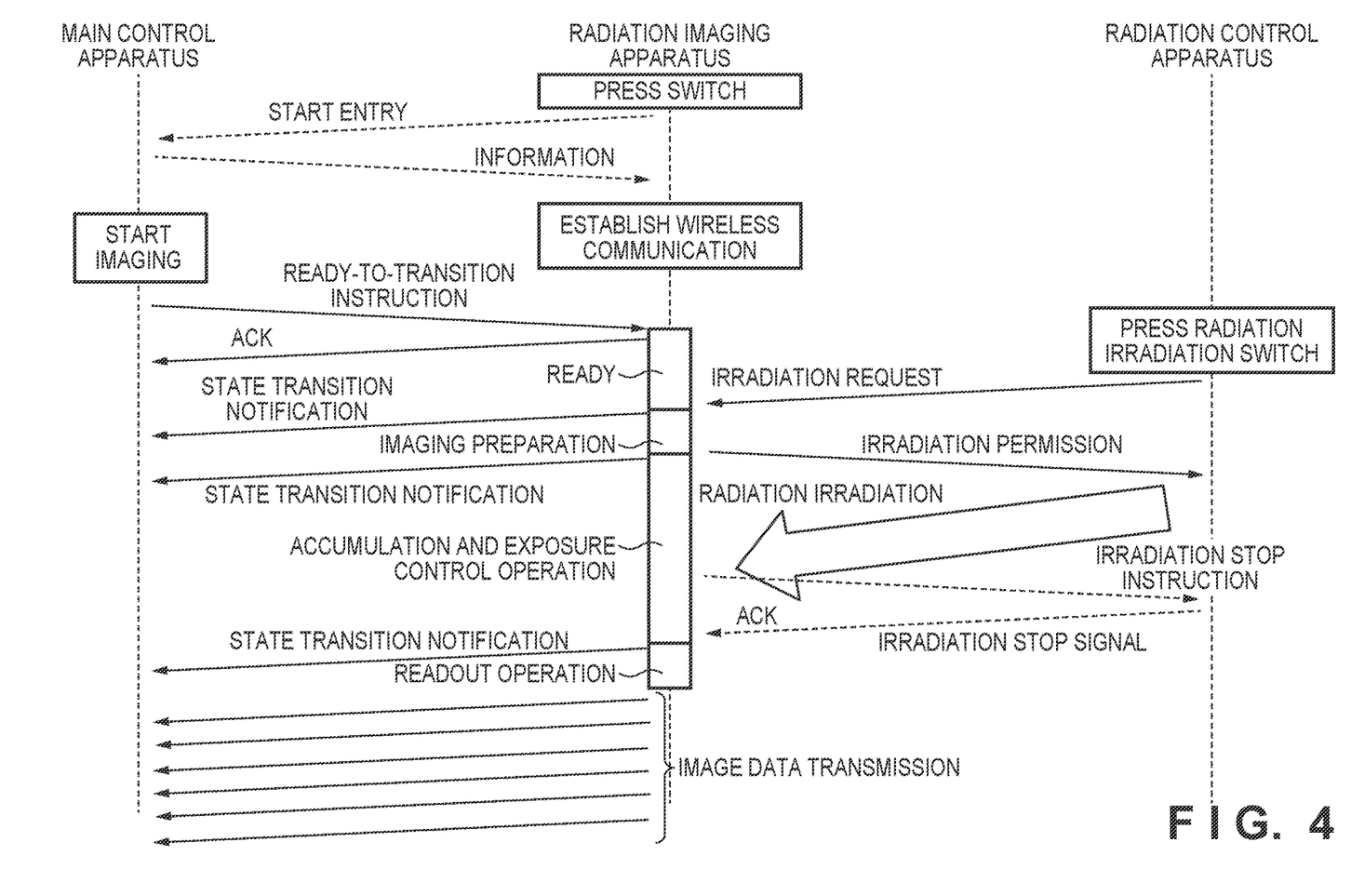
FIG. 4 is a timing chart illustrating a imaging operation of the radiation imaging system of FIG. 1.

FIG. 4 is a timing chart illustrating operation of the present embodiment. In the drawing, the solid arrows represent communication via the wireless communication unit 302 and the wireless access point 320 and the dashed arrows represent communication via the wireless communication unit 302 and the entry apparatus 322 or the wireless communication unit 302 and the wireless unit 326. By the operator 312 pressing the switch 303 of the radiation imaging apparatus 300, the operation of registering (entry operation) into the radiation imaging system 10 the radiation imaging apparatus 300 is started. Between the radiation imaging apparatus 300 and the main control apparatus 310, the setting information and the apparatus information are transmitted via the wireless communication unit 302 and the entry apparatus 322 as described above. By this, communication via the wireless communication unit 302 and the wireless access point 320 between the radiation imaging apparatus 300 and the main control apparatus 310 is established. Also, communication between the wireless communication unit 302 of the radiation imaging apparatus 300 and the wireless unit 326 of the radiation control apparatus 324 is established.

The operator 312, when starting imaging, by operating the main control apparatus 310, the display apparatus 313, and the input apparatus 314 and selecting/pressing switches on the GUI and the like, issues an instruction to start imaging. This instruction passes through the wireless access point 320 and the wireless communication unit 302 and is transmitted to the radiation imaging apparatus 300 as a command instructing to transition into a ready state. The ready state refers to a state in which, by supplying power from the power supply control unit 301 to the radiation detector 100, the drive circuit 221, the drive circuit 241, and the like and conducting preparation driving and the like, the radiation imaging apparatus 300 can conduct imaging. Here, the radiation imaging apparatus 300 returns a response (ACK) as appropriate in relation to the command received from the main control apparatus 310. That the radiation imaging apparatus 300 has entered the ready state is notified to the operator 312 by the GUI of the display apparatus 313, a display device (not shown) disposed in the radiation imaging apparatus 300, and the like.

The operator 312, after finishing the setting of the subject 306 and the radiation imaging apparatus 300, presses the radiation irradiation switch 311. In response to the pressing of the radiation irradiation switch 311, the radiation control apparatus 324 transmits to the radiation imaging apparatus 300 an irradiation request via the interface box 323 and the wireless access point 320. The radiation imaging apparatus 300, upon receiving the irradiation request, performs an imaging preparation operation. When the imaging preparation operation is completed, the radiation imaging apparatus 300 transmits to the radiation control apparatus 324 an irradiation permission signal via the wireless access point 320 or the wireless unit 326, the imaging pixels 101 disposed in the imaging region transitions to an accumulation state, and then an exposure control operation using the detection pixels 121, which are a detection unit, is started. The radiation imaging apparatus 300 notifies to the main control apparatus 310 that a transition of states has occurred.

The radiation control apparatus 324, upon receiving the irradiation permission signal, starts radiation irradiation onto the radiation source 325. The radiation imaging apparatus 300 performs the above exposure control and then transmits to the radiation control apparatus 324 via the wireless unit 326 a signal instructing to stop radiation irradiation. The radiation control apparatus 324, upon receiving the signal instructing to stop irradiation, causes the radiation source 325 to stop the radiation irradiation and then transmits to the radiation imaging apparatus 300 an irradiation stop signal (ACK) indicating that radiation irradiation has been stopped via the wireless unit 326. In response to the irradiation stop signal, the radiation imaging apparatus 300 ends the accumulation operation in the imaging pixels 101 and exposure control that uses the detection pixels 121, reads out the charge accumulated in the imaging pixels 101, and then generates radiation image data. Then the radiation imaging apparatus 300 transmits to the main control apparatus 310 the radiation image data via the wireless communication unit 302 and the wireless access point 320. Here, the signal instructing to stop radiation irradiation and the irradiation stop signal were described to be transmitted via the wireless communication unit 302 of the radiation imaging apparatus 300 and the wireless unit 326 of the radiation control apparatus 324; however, the present invention is not limited to this. The signal instructing to stop radiation irradiation and the irradiation stop signal may be transmitted via the wireless communication unit 302, the wireless access point 320, and the interface box 323.

Here, in a case where a problem arises in the communication between the radiation imaging apparatus 300 and the radiation control apparatus 324 when transmitting the signal instructing to stop radiation irradiation to the radiation control apparatus 324 from the radiation imaging apparatus 300, the following problems will arise. In a case where the arrival of the signal instructing to stop radiation irradiation is delayed, unnecessary radiation is irradiated onto the subject 306. Also, in a case where the signal does not arrive, there is a possibility that an artifact is generated in an image due to the exposure control function not operating and then the timings to stop radiation irradiation and to read out the charge accumulated in the imaging pixels 101 not matching. Also, there is a possibility that the quality of radiation images to be acquired will decrease, such as with overexposure, due to the exposure control function not operating and then radiation that is more than an appropriate amount being inputted into the radiation imaging apparatus 300.

Also, cases where an irradiation stop signal indicating that radiation irradiation has been stopped is not received from the radiation control apparatus due to a problem in the communication between the radiation imaging apparatus 300 and the radiation control apparatus 324 are conceivable. In other words, these are cases in which an irradiation stop signal to the radiation imaging apparatus 300 from the radiation control apparatus 324 does not arrive even though the signal instructing to stop radiation irradiation to the radiation control apparatus 324 from the radiation imaging apparatus 300 is delivered successfully. In such cases, there is a possibility that the quality of a radiation image to be acquired will decrease due to unnecessary waiting time occurring after stopping radiation irradiation, a readout of the charge accumulated in the imaging pixels 101 not being able to start, and then unnecessary background noise being accumulated in the imaging pixels 101.

To prevent such problems, the signals instructing to stop radiation irradiation from the radiation imaging apparatus 300 to the radiation control apparatus 324 and the irradiation stop signals from the radiation control apparatus 324 to the radiation imaging apparatus 300, which relate to exposure control, need to be reliably transmitted. A method of more reliably transmitting signals that relate to exposure control using wireless communication between the radiation imaging apparatus 300 and the radiation control apparatus 324 will be described with reference to FIG. 5.

Figure 5:
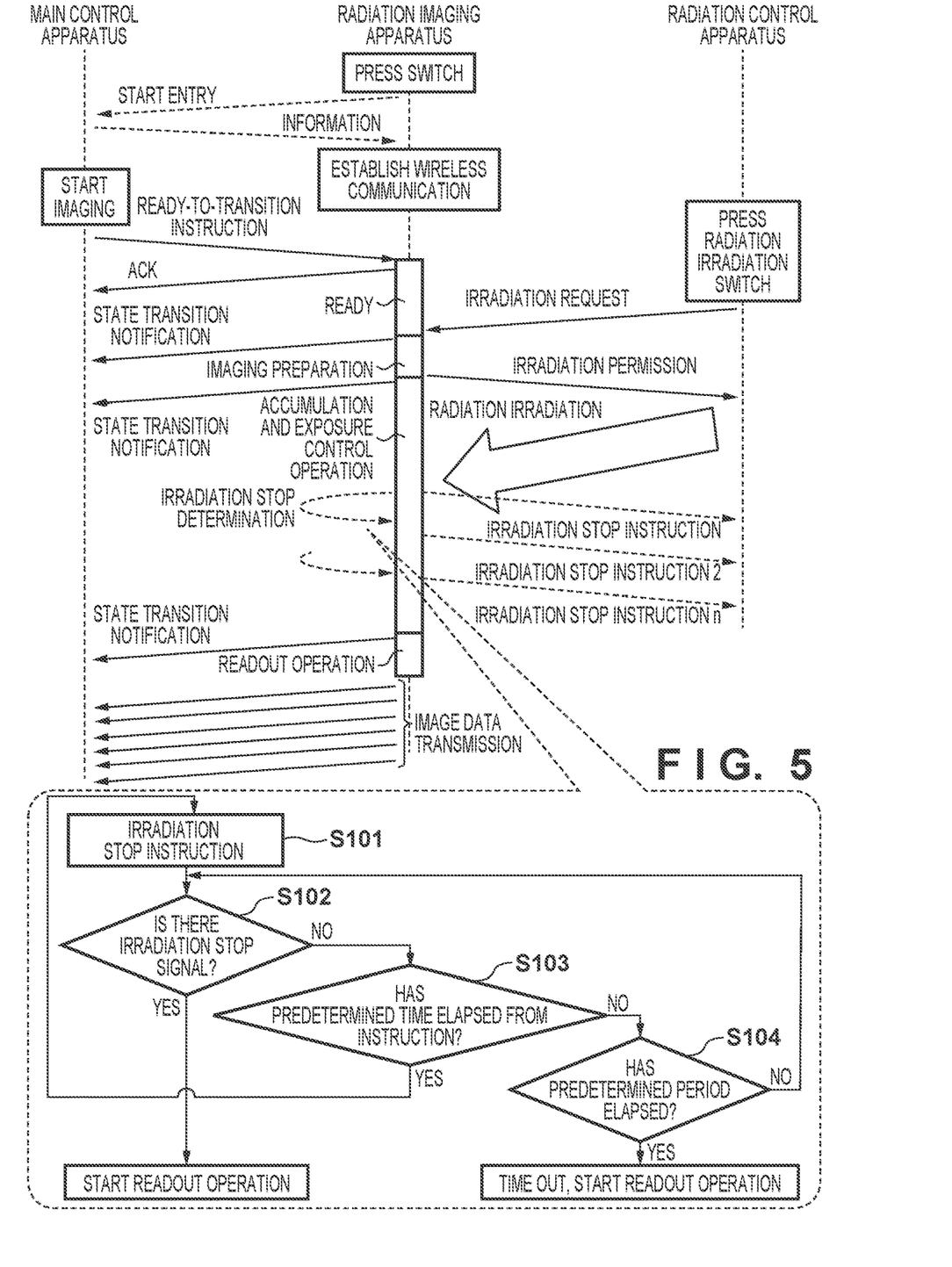
FIG. 5 is a timing chart illustrating a imaging operation of the radiation imaging system of FIG. 1.

As described above, by an irradiation stop signal (irradiation stop ACK) arriving from the radiation control apparatus 324, the radiation imaging apparatus 300 starts a readout operation that reads out from a plurality of pixels (the imaging pixels 101) the radiation image data. However, in a case where the irradiation stop signal is not received, the radiation imaging apparatus 300 cannot start the readout operation in a normal operation. Accordingly, the radiation imaging apparatus 300, in a case where the irradiation stop signal indicating that radiation irradiation has been stopped is not received from the radiation control apparatus 324 after a signal instructing to stop radiation irradiation has been transmitted to the radiation control apparatus 324 and until a first time interval has elapsed from when the signal instructing to stop radiation irradiation has been transmitted, transmits a signal instructing to stop radiation irradiation to the radiation control apparatus 324 again. As illustrated in FIG. 5, in step S101, the radiation imaging apparatus 300 transmits to the radiation control apparatus 324 a signal instructing to stop radiation irradiation. Next, in a case where an irradiation stop signal is received from the radiation control apparatus 324 (YES in step S102), the radiation imaging apparatus 300 starts a readout operation. In a case where the irradiation stop signal is not received from the radiation control apparatus 324, the radiation imaging apparatus 300, after a predetermined time has elapsed, transmits to the radiation control apparatus 324 the signal instructing to stop radiation irradiation again (NO in step S102, YES in step S103). For example, the radiation imaging apparatus 300, in a case where the irradiation stop signal is not received, performs retransmission of the signal instructing to stop radiation irradiation every 10 milliseconds.

For example, the radiation imaging apparatus 300, after a first time interval has elapsed, may transmit the signal instructing to stop radiation irradiation to the radiation control apparatus 324 every second time interval until the irradiation stop signal is received. However, depending on communication conditions, the radiation imaging apparatus 300 may not be able to receive the irradiation stop signal. Accordingly, in a case, for example, where the predetermined period has elapsed, the radiation imaging apparatus 300 may time out the imaging of a radiation image and start a readout operation (NO in step S104). For example, the radiation imaging apparatus 300, after a first time interval has elapsed and in a period until an accumulation time that has been set in advance for the plurality of pixels (the imaging pixels 101) elapses, may transmit the signal instructing to stop radiation irradiation to the radiation control apparatus 324 every second time interval until the irradiation stop signal is received.

In such a case, the radiation imaging apparatus 300, in a case where the irradiation stop signal is received in the period until the accumulation time elapses, may start the readout operation that reads out from the plurality of pixels (the imaging pixels 101) the radiation image data in response to receiving the irradiation stop signal. Meanwhile, the radiation imaging apparatus 300, in a case where the irradiation stop signal is not received, may start the readout operation that reads out from the plurality of pixels (the imaging pixels 101) the radiation image data after the accumulation time has elapsed. Also, for example, the radiation imaging apparatus 300, irrespective of whether or not the irradiation stop signal is received, may start a readout operation that reads out from the plurality of pixels (the imaging pixels 101) the radiation image data after the accumulation time has elapsed.

Here, the first time interval of waiting from when the signal instructing to stop radiation irradiation is first transmitted until the irradiation stop signal is received and the second time interval in which retransmission of the signal instructing to stop radiation irradiation is repeated thereafter may be the same or different. Also, the second time may be a constant or may change in a period that the transmission of the signal instructing to stop radiation irradiation is repeated. Also, for example, the detection unit that uses the detection pixels 121 may detect the start of radiation irradiation, and the radiation imaging apparatus 300, after transmitting the signal instructing to start radiation irradiation to the radiation control apparatus 324, may control the first time interval based on the time it takes for the detection unit to detect the start of radiation irradiation. Similarly, the radiation imaging apparatus 300 may control the second time interval based on the time it takes from when the signal instructing to start radiation irradiation was transmitted to the radiation control apparatus 324 until the detection unit detects the start of radiation irradiation. Also, for example, the radiation imaging apparatus 300 may control the first time interval and the second time interval based on a time interval of communication between the radiation imaging apparatus 300 and the radiation control apparatus 324 measured in advance before imaging the radiation image. For example, in a case where the wireless communication environment is poor based on the time interval of communication between the radiation imaging apparatus 300 and the radiation control apparatus 324 (in a case where the communication time interval is long), the above second time interval may be made shorter than in a case where the wireless communication environment is good. In this case where the wireless communication environment is poor, the above first time interval may be made longer or shorter than in a case where the wireless communication environment is good. Also, for example, in a case where the wireless communication environment is poor, the radiation imaging apparatus 300 does not need to perform retransmission of the signal instructing to stop radiation irradiation and may wait until the accumulation time elapses.

In the above, setting the exposure control time out based on the accumulation time was described; however, the present invention is not limited to this. In a case where the detection unit that uses the detection pixels 121 can detect the stop of radiation irradiation, the radiation imaging apparatus 300, after the first time interval has elapsed and in a period until the detection unit detects the stop of radiation irradiation, may transmit the signal instructing to stop radiation irradiation to the radiation control apparatus 324 every second time interval until the irradiation stop signal is received. In such a case, the radiation imaging apparatus 300, in a case where the irradiation stop signal is received in the period until the detection unit detects the stoppage of radiation irradiation, may start the readout operation that reads out, from the plurality of pixels (the imaging pixels 101), the radiation image data in response to receiving the irradiation stop signal. Meanwhile, the radiation imaging apparatus 300, in a case where the irradiation stop signal is not received, may start the readout operation that reads out, from the plurality of pixels (the imaging pixels 101), the radiation image data after the detection unit detects the stoppage of radiation irradiation. Also, for example, the radiation imaging apparatus 300, irrespective of whether the irradiation stop signal is received, may start the readout operation that reads out from a plurality of pixels (the imaging pixels 101) the radiation image data after the detection unit has detected the stop of radiation irradiation.

Furthermore, the accumulation time and the stop and detection of radiation irradiation by the detection unit may be combined. In other words, the radiation imaging apparatus 300, after the first time interval has elapsed, in a period until the accumulation time has elapsed or detection of the stop of radiation irradiation by the detection unit, whichever event occurs first, may transmit the signal instructing to stop radiation irradiation to the radiation control apparatus every second time interval until the irradiation stop signal is received. In such a case, the radiation imaging apparatus 300, in a case where the irradiation stop signal is received in the period until the above-described event occurs, may start the readout operation that reads out from the plurality of pixels (the imaging pixels 101) the radiation image data in response to receiving the irradiation stop signal. Meanwhile, the radiation imaging apparatus 300, in a case where the irradiation stop signal is not received, may start the readout operation that reads out from the plurality of pixels (the imaging pixels 101) the radiation image data after the above-described event occurred. Also, for example, the radiation imaging apparatus 300, irrespective of whether or not the irradiation stop signal is not received, may start the readout operation that reads out from the plurality of pixels (the imaging pixels 101) the radiation image data after the above-described event has occurred.

In the present embodiment, the radiation imaging apparatus 300, in a case where the irradiation stop signal is not received from the radiation control apparatus 324, retransmits to the radiation control apparatus 324 the signal instructing to stop radiation irradiation. In other words, at least until the irradiation stop signal is received from an external apparatus such as the radiation control apparatus 324, the signal instructing to stop radiation irradiation is retransmitted to the external apparatus. By this, in the radiation imaging system 10 that performs exchange of signals for exposure control using wireless communication, even in a case where there is a problem in the communication, it becomes possible to prevent a decrease in exposure control accuracy. By this, it becomes possible to stably perform imaging that uses exposure control in wireless communication environments where conditions can always change. As a result, it is possible to reduce unnecessary radiation exposure related to the subject 306 and also prevent a decrease in the quality of radiation images to be acquired. In other words, the radiation imaging apparatus 300 and the radiation imaging system 10 that are user-friendly can be realized.

In the above, the case here the signal instructing to stop radiation irradiation from the radiation imaging apparatus 300 to the radiation control apparatus 324 and the case where the irradiation stop signal from the radiation control apparatus 324 to the radiation imaging apparatus 300 did not arrive were described. Meanwhile, in a case where the irradiation permission signal from the radiation imaging apparatus 300 to the radiation control apparatus 324 similarly does not arrive in the radiation control apparatus 324, radiation is not irradiated from the radiation source 325 and, for example, a wait will occur until the time out of the accumulation time of the radiation imaging apparatus 300. Accordingly, for example, the detection unit that uses the detection pixels 121 may detect the start of radiation irradiation, and the radiation imaging apparatus 300, after transmitting the signal instructing to start radiation irradiation to the radiation control apparatus 324, and until a third time interval has elapsed from the transmission of the signal instructing to start radiation irradiation, may transmit a signal instructing to start radiation irradiation to the radiation control apparatus 324 again in the case where the detection unit to detect the start of radiation irradiation. By this, a case where the wireless communication environment worsens and imaging is not executed can be prevented, and the radiation imaging apparatus 300 and the radiation imaging system 10 that are more useful can be realized.

After imaging the radiation image, transmission of radiation image data may transmit the entire data at once. Also, a configuration may be taken such that by first transmitting thinned data from which some data was removed from the acquired radiation image data and then the main control apparatus 310 executing image processing, an image is displayed as fast as possible on the display apparatus 313. Also, in preparation for a case where the wireless communication environment worsens and the radiation image data cannot be transmitted, a case where it takes a lot of time, and the like, the radiation image data may be held in the non-volatile memory 402 in the radiation imaging apparatus 300.

The setting of the wireless communication unit 302 of the radiation imaging apparatus 300 set for the radiation imaging apparatus 300 by the registration operation (entry operation) may be held in the memory 402 in the radiation imaging apparatus 300. By this, it becomes unnecessary to perform another registration operation (entry operation) for when the radiation imaging apparatus 300 is turned on again after having been turned off.

In a case of operating the radiation imaging apparatus 300 at a facility such as a hospital that has a plurality of systems similar to the radiation imaging system 10 in addition to the radiation imaging system 10, there are cases where the radiation imaging apparatus 300 is brought and used in a radiation imaging system different from the radiation imaging system 10. In a case where the radiation imaging apparatus 300 is brought into another system, an operation for registering (entry operation) the radiation imaging apparatus 300 into another system is conducted again. By this, information for establishing communication via the wireless communication unit 302 of the radiation imaging apparatus 300 in a new system can be acquired. The information for establishing wireless communication may be overwritten every time the registration operation (entry operation) is performed so that only one pieces of information is held in the memory 402 of the radiation imaging apparatus 300, or a plurality of pieces of information may be held.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2020-98882, filed Jun. 5, 2020, which is hereby incorporated by reference herein in its entirety.

What is claimed is:

1. A radiation imaging system comprising:
  a radiation imaging apparatus including a plurality of pixels for acquiring radiation image data and a detection unit for performing exposure control during radiation irradiation; and a radiation control apparatus configured to control a radiation source that irradiates radiation to the radiation imaging apparatus, wherein
  the radiation imaging apparatus and the radiation control apparatus transmit signals that relate to exposure control by wireless communication, and
  the radiation imaging apparatus, in a case where an irradiation stop signal indicating that radiation irradiation has been stopped is not received from the radiation control apparatus after a signal instructing to stop radiation irradiation has been transmitted to the radiation control apparatus and until a first time interval has elapsed, transmits a signal instructing to stop radiation irradiation to the radiation control apparatus again.

2. The radiation imaging system according to claim 1, wherein the radiation imaging apparatus, after the first time interval has elapsed, transmits a signal instructing to stop radiation irradiation to the radiation control apparatus every second time interval until the irradiation stop signal is received.

3. The radiation imaging system according to claim 1, wherein the radiation imaging apparatus, after the first time interval has elapsed and in a period until an accumulation time that has been set in advance for the plurality of pixels elapses, transmits a signal instructing to stop radiation irradiation to the radiation control apparatus every second time interval until the irradiation stop signal is received.

4. The radiation imaging system according to claim 3, wherein the radiation imaging apparatus, irrespective of whether the irradiation stop signal is received, starts a readout operation that reads out from the plurality of pixels the radiation image data after the accumulation time has elapsed.

5. The radiation imaging system according to claim 3, wherein
  the radiation imaging apparatus, in a period until the accumulation time elapses,
  in a case where the irradiation stop signal is received, starts a readout operation that reads out from the plurality of pixels the radiation image data in response to the reception of the irradiation stop signal, and
  in a case where the irradiation stop signal is not received, starts a readout operation that reads out from the plurality of pixels the radiation image data after the accumulation time has elapsed.

6. The radiation imaging system according to claim 3, wherein
  the detection unit detects a stoppage of radiation irradiation, and
  the radiation imaging apparatus, after the first time interval has elapsed, in a period until the accumulation time has elapsed or the detection of the stoppage of radiation irradiation by the detection unit, whichever event occurs first, transmits a signal instructing to stop radiation irradiation to the radiation control apparatus every second time interval until the irradiation stop signal is received.

7. The radiation imaging system according to claim 6, wherein the radiation imaging apparatus, irrespective of whether the irradiation stop signal is received, starts a readout operation that reads out from the plurality of pixels the radiation image data after the event has occurred.

8. The radiation imaging system according to claim 6, wherein
  the radiation imaging apparatus, in a period until the event has occurred,
  in a case where the irradiation stop signal is received, starts a readout operation that reads out from the plurality of pixels the radiation image data in response to the reception of the irradiation stop signal, and
  in a case where the irradiation stop signal is not received, starts a readout operation that reads out from the plurality of pixels the radiation image data after the event has occurred.

9. The radiation imaging system according to claim 1, wherein
the detection unit detects a stoppage of radiation irradiation, and
the radiation imaging apparatus, after the first time interval has elapsed, in a period until the detection unit detects a stoppage of radiation irradiation, transmits a signal instructing to stop radiation irradiation to the radiation control apparatus every second time interval until the irradiation stop signal is received.

10. The radiation imaging system according to claim 9, wherein the radiation imaging apparatus, irrespective of whether the irradiation stop signal is received, starts a readout operation that reads out from the plurality of pixels the radiation image data after the detection unit has detected a stoppage of radiation irradiation.

11. The radiation imaging system according to claim 9, wherein
the radiation imaging apparatus, in a period until the detection unit detects a stoppage of radiation irradiation,
in a case where the irradiation stop signal is received, starts a readout operation that reads out from the plurality of pixels the radiation image data in response to the reception of the irradiation stop signal, and
in a case where the irradiation stop signal is not received, starts a readout operation that reads out from the plurality of pixels the radiation image data after the detection unit has detected a stoppage of radiation irradiation.

12. The radiation imaging system according to claim 2, wherein the first time interval and the second time interval are the same length.

13. The radiation imaging system according to claim 1, wherein
the detection unit detects a start of radiation irradiation, and
the radiation imaging apparatus controls the first time interval based on a time it takes from when a signal instructing to start radiation irradiation was transmitted to the radiation control apparatus until the detection unit detects the start of radiation irradiation.

14. The radiation imaging system according to claim 2, wherein
the detection unit detects a start of radiation irradiation, and
the radiation imaging apparatus controls the first time interval and the second time interval based on a time it takes from when a signal instructing to start radiation irradiation was transmitted to the radiation control apparatus until the detection unit detects the start of radiation irradiation.

15. The radiation imaging system according to claim 1, wherein the radiation imaging apparatus controls the first time interval based on a time interval of communication between the radiation imaging apparatus and the radiation control apparatus measured in advance.

16. The radiation imaging system according to claim 2, wherein the radiation imaging apparatus controls the first time interval and the second time interval based on a time interval of communication between the radiation imaging apparatus and the radiation control apparatus measured in advance.

17. The radiation imaging system according to claim 1, wherein
the detection unit detects a start of radiation irradiation, and
the radiation imaging apparatus, in a case where the detection unit does not detect a start of radiation irradiation after a signal instructing to start radiation irradiation has been transmitted to the radiation control apparatus and until a third time interval has elapsed, transmits a signal instructing to start radiation irradiation to the radiation control apparatus again.

18. The radiation imaging system according to claim 1, wherein the wireless communication is communication that uses a wireless LAN.

19. The radiation imaging system according to claim 1, wherein
the radiation imaging apparatus includes an imaging region in which the plurality of pixels are disposed, and
the detection unit is disposed in the imaging region.

20. A radiation imaging apparatus comprising:
a plurality of pixels for acquiring radiation image data; and a detection unit for performing exposure control during radiation irradiation, wherein
the radiation imaging apparatus, in a case where an irradiation stop signal indicating that radiation irradiation has been stopped is not received from an external apparatus after a signal instructing to stop radiation irradiation has been transmitted to the external apparatus by wireless communication and until a first time interval has elapsed, transmits a signal instructing to stop radiation irradiation to the external apparatus again.

* * * * *